United States Patent [19]

Shiono et al.

[11] 4,252,726

[45] Feb. 24, 1981

[54] PREPARATION OF DL-α-TOCOPHEROL

[75] Inventors: Manzo Shiono; Yoichi Ninagawa, both of Kurashiki; Yoshiaki Omura, Okayama, all of Japan

[73] Assignee: Kuraray Co., Ltd., Japan

[21] Appl. No.: 2,892

[22] Filed: Jan. 12, 1979

[30] Foreign Application Priority Data

Jan. 12, 1978 [JP] Japan .................................. 53-2556

[51] Int. Cl.³ .......................................... C07D 311/72
[52] U.S. Cl. ................................................. 260/345.5
[58] Field of Search ..................................... 260/345.5

[56] References Cited

U.S. PATENT DOCUMENTS

| 3,455,959 | 7/1969 | Mayer et al. | 260/345.5 |
| 3,651,113 | 3/1972 | Metlesics et al. | 260/345.5 |
| 3,789,086 | 1/1974 | Frick et al. | 260/345.5 |

FOREIGN PATENT DOCUMENTS

| 45-31662 | 10/1970 | Japan | 260/345.5 |
| 48-91075 | 11/1973 | Japan | 260/345.5 |
| 49-27187 | 7/1974 | Japan | 260/345.5 |

OTHER PUBLICATIONS

Eisai, Derwent No. 65663Y, 1-28-76.

*Primary Examiner*—Nicky Chan
*Attorney, Agent, or Firm*—Burns, Doane, Swecker & Mathis

[57] ABSTRACT dl-α-Tocopherol is prepared by condensing trimethylhydroquinone with phytyl halide in a chlorinated lower aliphatic hydrocarbon solvent, in the presence of metallic tin and a Friedel-Crafts catalyst.

12 Claims, No Drawings

PREPARATION OF DL-α-TOCOPHEROL

BACKGROUND OF THE INVENTION

1. Field of the Invention

The present invention relates to a novel method for preparing di-α-tocopherol comprising condensing trimethylhydroquinone with phytyl halide in a chlorinated lower aliphatic hydrocarbon solvent in the presence of metallic tin and a Friedel-Crafts catalyst.

2. Description of Prior Art

Typically, dl-α-tocopherol is prepared by condensing trimethyl hydroquinone [hereunder referred to as "TMHQ"] with isophytol, phytol or phytyl halide in the presence of a Friedel-Crafts catalyst. Such condensation, however, entails concurrent side reactions, such as oxidation, which tends to give rise to formation of colored impurities, and generally results in production of colored dl-α-tocopherol. It is therefore necessary to separate and remove such colored impurities in order to utilize the dl-α-tocopherol practically, e.g., in the pharmaceutical field. However, such colored impurities formed have physical properties similar to those of dl-α-tocopherol, wherefore complete separation and removal thereof by high vacuum distillation or molecular distillation is rendered difficult. Furthermore, such purifications require highly sophisticated refining means. It is, therefore, of the utmost importance in the manufacture of dl-α-tocopherol on an industrial scale to establish reaction conditions which minimize the formation of such colored impurities during the condensation reaction.

With a view towards the immediately aforesaid, various preparations and syntheses have been studied to provide dl-α-tocopherol with less coloring. For example, proposed have been:

[i] Condensation of TMHQ and phytyl halide in a petroleum hydrocarbon system, such as ligroin, petroleum benzine, hexane, etc., in the presence of metallic zinc [cf. Japanese Patent Publication No. 31662/70; the Comparative Example 1 which follows];

[ii] Condensation of TMHQ and phytol, isophytol or phytyl halide in an organic solvent such as ethyl acetate, isopropyl ether, etc., in the presence of an acidic catalyst such as zinc chloride, aluminum chloride, boron trifluoride etherate, sulfuric acid, formic acid, stannous chloride, with addition of metal powder selected from among aluminum, iron or tin [cf. Japanese Patent Publication No. 27187/74; the comparative Example 2 which follows];

[iii] Condensation of TMHQ and phytyl halide in a non-polar organic solvent such as petroleum ether, hexane, petroleum benzine, ligroin, benzene, toluene, ether, etc., in the presence of a Friedel-Crafts catalyst and metallic tin [cf. Japanese published Patent Application No. 91075/73; the Comparative Example 3 which follows].

Above noted methods [i], [ii] and [iii] and modifications of the method [iii] [cf. Comparative Examples 4 and 5 which follow], however, are not appropriate or suitable for manufacturing dl-α-tocopherol on an industrial scale, either because the product obtained thereby is still highly colored for practical use in the pharmaceutical field, or because the yield is unsatisfactorily low.

SUMMARY OF THE INVENTION

Accordingly, a primary object of the present invention is to provide a method for manufacturing a more highly pure and less colored di-α-tocopherol in an easy manner, and in high yields.

Briefly, it has now surprisingly been determined that a certain solvent enables attainment of the objects of the invention via condensation between TMHQ and phytyl halide, and utilizing a combination of metallic tin and a Friedel-Crafts catalyst as the catalyst system. It is thus possible to efficiently promote the basic reaction through use of chlorinated lower aliphatic hydrocarbons as the reaction solvent, while effectively suppressing side reactions such as any oxidation reaction, and whereby a less colored dl-α-tocopherol having a greater purity is obtained in high yield, as compared with that obtained via the conventional known methods.

DETAILED DESCRIPTION OF THE INVENTION

According to the present invention, the presence of chlorinated lower aliphatic hydrocarbons in the condensation reaction medium gives rise to uniform dispersion of the metallic tin therein. This facilitates the formation of nascent hydrogen as the active surface of said metallic tin contacts the hydrogen halide which is formed during the reaction. It is considered that the reducing power of said nascent hydrogen stabilizes not only the reaction raw materials, i.e., TMHQ, but also the tocopheryl hydroquinone which is a reaction intermediate and the dl-α-tocopherol which is the reaction product, and whereby side reactions such as oxidation, as well as the formation of colored impurities, are not only inhibited, but the main reaction is even efficiently promoted.

Preferred chlorinated lower aliphatic hydrocarbon solvents employed in accordance with the present invention are polychlorinated hydrocarbon solvents having 1 to 2 carbons, whether used alone or in any combination, such as 1,2-dichloroethane [hereinafter referred to as dichloroethane], 1,1,2,2-tetrachloroethane, 1,2-dichloroethylene, 1,1,2-trichloroethylene [hereinafter referred to as trichlene], 1,1,2,2-tetrachloroethylene, chloroform, carbon tetrachloride, methylene chloride, and the like; dichloroethane and trichlene are the more preferred. The preferred amount of solvent is in the range of about 2 to 100 times the weight of the TMHQ and, more preferably, about 5 to 20 times the weight of the TMHQ.

The preferred Friedel-Crafts catalysts are zinc chloride, aluminum chloride, boron trifluoride etherate, iron chloride and tin chloride; the amount thereof to be used is in the range of 0.001 to 0.1 mol equivalent of the TMHQ, and, more preferably, a very small amount of 0.001 to 0.02 times the mol volume of the TMHQ is sufficient. Metallic tin to be utilized is preferably as fine a powder as possible, the amount thereof being in the range of 0.02 to 1.0 mol equivalent of the TMHQ, and, more preferably, 0.05 to 0.4 times the mol volume. Metallic tin is added to the reaction system continuously or intermittently over several additions by dividing the required amount into smaller portions. The unreacted metallic tin may be recovered and reused by washing same with the reaction solvent of the present invention, or other organic solvents such as acetone, benzene and ethyl acetate, water or diluted acid.

The condensation reaction is advantageously carried out at a temperature in the range of 40° to 150° C.

In a preferred example of the present invention, TMHQ and metallic tin and a Friedel-Crafts catalyst are dissolved in a chlorinated lower aliphatic hydrocarbon solvent. The reaction system is agitated and refluxed in an atmosphere of inert gas, such as nitrogen, while phytyl halide in a substantially equimolecular amount of the TMHQ is added to said reaction system over a period of from about 0.5 to 8 hours. After the addition of the phytyl halide, the agitation is continued for another about 0.5 to 4 hours, to obtain a colorless or pale yellow reaction mixture containing the dl-α-tocopherol. After the solvent is distilled off from said reaction mixture, n-hexane or the like is added to the residue and the resulting solution is washed with water, and an aqueous methanolic solution of sodium hydrosulfite, or an aqueous methanolic solution of dilute alkali or the like, and then subjected to concentration under reduced pressure to obtain a crude dl-α-tocopherol fraction. Because said dl-α-tocopherol contains substantially no colored impurities, it is subjected to molecular distillation, high vacuum distillation, or the like. By removing a small amount of initial and final distillation fractions, a dl-α-tocopherol which displays high purity but less coloring can be obtained in high yield. If desired, it is also possible to quantatively convert the dl-α-tocopherol in the above-mentioned reaction mixture to dl-α-tocopheryl acetate by subjecting the reaction mixture to agitation and reflux for about 1 to 5 hours with the addition of 1 to 8 mol equivalents of acetic anhydride, 0.1 to 1 mol equivalents of pyridine, picoline or sodium acetate, the amount being based on 1 mol of TMHQ.

Lower boiling fractions, such as solvent, etc., are removed from the reaction mixture which contains the dl-α-tocopheryl acetate in a similar manner to that described above for dl-α-tocopherol. The reaction mixture is added to n-hexane or the like and such solution is washed with water, or an aqueous solution of sodium hydrosulfite, or the like. It is then subjected to concentration under reduced pressure to obtain crude dl-α-tocopheryl acetate, which is subjected to molecular distillation, high vacuum distillation, etc., to obtain dl-α-tocopheryl acetate with less coloring and high purity. Both the condensation and acetylation reactions can be carried out continuously.

In order to further illustrate the present invention and the advantages thereof, the following specific examples and comparative examples are given, it being understood with respect to said examples according to the invention that same are intended only as illustrative and in nowise limitative.

The degree of coloring of the dl-α-tocopheryl acetate is expressed in absorbance E which is measured by a spectrophotometer [manufactured by Hitachi Ltd., Model 100-10]; dl-α-tocopheryl acetate is placed in a quartz cell [1 cm×1 cm] in the form of either an oil or 40% ethanolic solution and absorbance E at 430 mμ for oil and 415 mμ for ethanolic solution, respectively, are measured and compared with the respective blank values [ethanol]. The values are referred to as $E_{430\ m\mu}^{neat}$ and $E_{415\ m\mu}^{40\%\ EtOH}$.

TMHQ and phytyl chloride used in the examples were from the same lot.

COMPARATIVE EXAMPLE 1

2.283 g of TMHQ and 0.236 g of metallic zinc powder were suspended in 11.8 ml of ligroin in an atmosphere of nitrogen. A solution of 4.943 g of phytyl chloride [purity 95.7%] in 7.9 ml of ligroin was dripped into said suspension under agitation and refluxed for a period of 2 hours 15 minutes. The suspension was heated and subjected to reflux for another 3 hours to obtain a reaction mixture of dl-α-tocopherol. 11.5 ml of acetic anhydride and 0.218 g of γ-picoline were added to the reaction mixture, which was then refluxed for 5 hours, to obtain 7.118 g of dl-α-tocopheryl acetate which reflected a pale yellow coloring. The absorbance of this dl-α-tocopheryl acetate was determined to be $E_{415\ m\mu}^{40\%\ EtOH} = 0.098$. Estimation of the dl-α-tocopheryl acetate by high pressure liquid chromatography with the use of n-nonane as the standard substance indicated that its purity was 84.4% and the yield was 84.7%.

COMPARATIVE EXAMPLE 2

To a solution of 2.283 g of TMHQ and 6.013 g of phytyl chloride in 12.0 ml of ethyl acetate were added 0.075 g of metallic aluminum powder and 0.904 g of stannous chloride, and the mixture was agitated at 80° C. for 3 hours. At this stage, the metallic aluminum powder adhered to the walls of the reactor and the reaction mixture turned to reddish brown. The obtained dl-α-tocopherol was acetylated in the same manner as described in Comparative Example 1 without isolating said dl-α-tocopherol to produce 8.023 g of dl-α-tocopheryl acetate. The absorbance of this crude dl-α-tocopheryl acetate was measured: $E_{430\ m\mu}^{neat} = 0.982$, $E_{415\ m\mu}^{40\%\ EtOH} = 0.719$. Estimation of the crude dl-α-tocopheryl acetate by liquid chromatography indicated that its purity was 84.2% and the yield was 95.3%.

COMPARATIVE EXAMPLE 3

2.283 g of TMHQ, 0.188 g of metallic tin powder and 0.019 g of boron trifluoride etherate were suspended in 19 ml of cyclohexane in an atmosphere of nitrogen. 5.515 g of phytyl chloride was dripped into said suspension over a period of 3 hours under agitation and reflux, and the reflux was continued for another 3 hours thereafter. To the reaction mixture was added 3.064 g of acetic anhydride and 0.613 g of sodium acetate, and the mixture was subjected to reflux for 2 hours. The reaction mixture obtained was introduced into ice water, neutralized with sodium carbonate, extracted with ligroin and dried. By concentrating and drying the reaction mixture, 7.320 g of dl-α-tocopheryl acetate which was almost achromatic was obtained. The absorbance of this crude dl-α-tocopheryl acetate was determined to be $E_{415\ m\mu}^{40\%\ EtOH} = 0.053$. Estimation of the crude dl-α-tocopheryl acetate by liquid chromatography indicated that its purity was 87.0% and the yield was 89.8%.

COMPARATIVE EXAMPLE 4

2.284 of TMHQ, 0.364 g of metallic tin powder and 0.133 g of zinc chloride were suspended in 15 ml of n-hexane in an atmosphere of nitrogen. A solution of 4.984 g of phytyl chloride in 10 ml of n-hexane was dripped into this suspension over a period of 2 hours under reflux. The suspension was subjected to reflux for another 2.5 hours to obtain a reaction mixture of dl-α-tocopherol. The obtained dl-α-tocopherol was acetylated in the same manner as described in Comparative Example 1 without isolating said dl-α-tocopherol to obtain 7.146 g of dl-α-tocopheryl acetate. The absorbance of this crude dl-α-tocopheryl acetate was measured: $E_{415\ m\mu}^{40\%\ EtOH} = 0.108$. Estimation of the crude dl-α-tocopheryl acetate by liquid chromatography indicated that its purity was 90.5% and the yield was 91.2%.

COMPARATIVE EXAMPLE 5

3.040 g of TMHQ, 0.484 g of metallic tin powder and 0.079 g of zinc chloride were suspended in 15 ml of ethyl acetate in an atmosphere of nitrogen. A solution of 7.975 g of phytyl chloride in 10 ml of ethyl acetate was dripped into said suspension over a period of 3 hours under heating and reflux. About 0.1 g metallic tin powder was added eight times, same amount per addition, in order to maintain said tin continuously suspended in the suspension. After addition of the phytyl chloride, the reaction mixture was subjected to heating and reflux for another 3 hours to obtain a reaction mixture of dl-α-tocopherol. The obtained dl-α-tocopherol was acetylated in the same manner as described in Comparative Example 1 without isolating said dl-α-tocopherol to obtain 10.454 of dl-α-tocopheryl acetate. The absorbance of this crude dl-α-tocopheryl acetate was measured: $E_{415\ m\mu}^{40\%\ EtOH} = 0.145$. Estimation of the crude dl-α-tocopheryl acetate by liquid chromatography indicated that its purity was 76.3% and the yield was 84.5%.

COMPARATIVE EXAMPLE 6

2.281 g of TMHQ and 0.040 of zinc chloride were suspended in 15 ml of dichloroethane in an atmosphere of nitrogen. A solution of 4.954 g of phytyl chloride in 10 ml of dichloroethane was dripped into said suspension over a period of 2.5 hours under heating and reflux, which was continued for another 3 hours to obtain a reaction mixture of dl-α-tocopherol. The obtained dl-α-tocopherol was acetylated in the same manner as described in Comparative Example 1 without isolating said dl-α-tocopherol to obtain 7.084 g of dl-α-tocopheryl acetate. The absorbance of this crude dl-α-tocopheryl acetate was measured: $E_{415\ m\mu}^{40\%\ EtOH} = 0.920$. Estimation of the crude dl-α-tocopheryl acetate by liquid chromatography indicated that its purity was 96.3% and the yield was 96.3%.

COMPARATIVE EXAMPLE 7

2.282 g of TMHQ and 0.202 g of metallic zinc powder were suspended in 15 ml of dichloroethane in an atmosphere of nitrogen. A solution of 4.942 g of phytyl chloride in 10 ml of dichloroethane was dripped into said suspension over a period of 3 hours under agitation and reflux. After the addition of 0.200 g of metallic zinc powder in 2.5 ml of dichloroethane to the above-obtained mixture, reflux was continued for another 2.5 hours to obtain a reaction mixture of dl-α-tocopherol. The obtained dl-α-tocopherol was acetylated in the same manner as described in Comparative Example 1 without isolating said dl-α-tocopherol to obtain 7.212 g of dl-α-tocopheryl acetate. The absorbance of this crude dl-α-tocopheryl acetate was measured: $E_{415\ m\mu}^{40\%\ EtOH} = 0.246$. Estimation of the crude dl-α-tocopheryl acetate by liquid chromatography indicated that its purity was 91.3% and the yield was 92.9%.

EXAMPLE 1

2.283 g of TMHQ, 0.356 g of metallic tin powder and 0.040 g of zinc chloride were suspended in 15 ml of dichloroethane in an atmosphere of nitrogen. A solution of 4.978 g of phytyl chloride in 10 ml of dichloroethane was dripped into said suspension over a period of 2.5 hours under agitation and reflux. After the addition of the metallic tin powder in an amount of 0.357 g to the suspension, reflux was continued for another 2.5 hours. When the reaction was terminated, the dichloroethane was distilled off under reduced pressure and n-hexane was added to the reaction mixture and the reaction mixture was filtered in an atmosphere of nitrogen. The hexane solution thus obtained was washed consecutively with water, aqueous methanolic solution (50:50) containing 1% sodium hydrosulfite, aqueous methanolic solution (50:50) containing 1% sodium hydroxide and water, dried and subjected to vacuum distillation to remove solvent, whereby 6.413 dl-α-tocopherol which was substantially achromatic was obtained. This crude dl-α-tocopherol was titrated with cerium ammonium sulfate; its purity was 96.5%. dl-α-tocopherol thus obtained was acetylated in the manner described in Comparative Example 1 to obtain dl-α-tocopheryl acetate. The absorbance of this crude dl-α-tocopheryl acetate was measured: $E_{415\ m\mu}^{40\%\ EtOH} = 0.039$.

EXAMPLE 2

2.281 g of TMHQ, 0.180 g of metallic tin powder and 0.044 of zinc chloride were suspended in 15 ml of dichloroethane. A solution of 4.943 g of phytyl chloride in 10 ml of dichloroethane was dripped into said suspension over a period of 2.5 hours under agitation and reflux in an atmosphere of nitrogen. After 0.360 g of metallic tin powder was added to the suspension, reflux was continued for another 3 hours. To the reaction mixture was then added 11.5 ml of acetic anhydride and 0.227 g of γ-picoline and the resulting mixture was subjected to reflux for 3 hours. When the reaction terminated, the reaction mixture was subjected to distillation under reduced pressure to remove dichloroethane, acetic acid and acetic anhydride. To the residue was added n-hexane and an aqueous solution of 2% sodium hydrosulfite, and the solution was filtered and separated. The hexane layer was washed 3 times with an aqueous solution of 2% sodium hydrosulfite and dried with anhydrous magnesium sulfate. The magnesium sulfate was filtered from the solution, which was concentrated to obtain 7.192 g of dl-α-tocopheryl acetate which was substantially achromatic. The absorbance of this dl-α-tocopheryl acetate was measured: $E_{415\ m\mu}^{40\%\ EtOH} = 0.036$. Estimation of dl-α-tocopheryl acetate by high pressure liquid chromatography with the use of n-nonane as the standard indicated that its purity was 95.7% and the yield was 97.1%.

EXAMPLE 3

22.8 g of TMHQ, 1.80 g of metallic tin powder and 0.44 g of zinc chloride were suspended in 150 ml of dichlorethane. A solution of 49.4 g of phytyl chloride in 100 ml of dichloroethane was dripped into said suspension over a period of 2.5 hours under agitation and refluxing. Reflux was continued for another 3 hours to obtain a reaction mixture of dl-α-tocopherol. The dl-α-tocopherol thus obtained was acetylated in the manner described in Example 2 without isolating the same to obtain 71.92 g of dl-α-tocopheryl acetate. The absorbance of this crude dl-α-tocopheryl acetate was measured: $E_{415\ m\mu}^{40\%\ EtOH} = 0.047$. Estimation of the crude dl-α-tocopheryl acetate by liquid chromatography indicated that its purity was 95.0% and the yield was 96.5%. Above crude dl-α-tocopheryl acetate was then subjected to molecular distillation [reduced pressure: $1.5 \times 10^{-3}$ mmHg] to obtain 65.20 g of dl-α-tocopheryl acetate [purity: 99.0%] which was achromatic and transparent.

dl-α-tocopheryl acetate thus obtained and the values of purity and yield determined by liquid chromatography estimation.

TABLE 1

| Example | TMHQ (g) | Metallic tin powder (g) | Friedel-Crafts catalyst (g) | Phytyl chloride | Metallic tin powder added (g) | crude dl-α-tocopheryl acetate yield (g) | purity (g) | yield (g) | $E_{415m\mu}^{40\% EtOH}$ |
|---|---|---|---|---|---|---|---|---|---|
| 5 | 2.284 | 0.364 | SnCl$_2$ 0.059 | 4.985 | 0.360 | 7.120 | 91.2 | 91.5 | 0.044 |
| 6 | 2.284 | 0.358 | AlCl$_3$ 0.045 | 4.988 | — | 7.097 | 92.3 | 92.3 | 0.046 |
| 7 | 2.284 | 0.356 | SnCl$_4$ 0.088 | 4.982 | 0.362 | 7.230 | 91.5 | 93.2 | 0.045 |
| 8 | 2.282 | 0.361 | BF$_3$·Et$_2$O 0.054 | 4.982 | 0.355 | 7.255 | 90.1 | 92.2 | 0.044 |

EXAMPLE 4

2.279 of TMHQ, 0.368 g of metallic tin powder and 0.041 g of zinc chloride were suspended in 15 ml of trichlene in an atmosphere of nitrogen. A solution of 4.939 g of phytyl chloride in 10 ml of trichlene was dripped into said suspension over a period of 2.5 hours under agitation and reflux. The reaction mixture was subjected to reflux under agitation for another 2 hours to obtain a reaction mixture containing dl-α-tocopherol which was substantially achromatic. To the reaction mixture was added 13.0 ml of acetic anhydride and 0.219 g of γ-picoline and the mixture was subjected to reflux for 2.5 hours. The lower boiling fractions were distilled off from the reaction mixture under reduced pressure. The reaction mixture was extracted with n-hexane in an amount of 50 ml, and the extract was washed 4 times with an aqueous solution of 2% sodium hydrosulfite, dried with anhydrous magnesium sulfate and concentrated under reduced pressure to obtain 7.167 g of dl-α-tocopheryl acetate which was a substantially achromatic viscous liquid. The absorbance of this crude dl-α-tocopheryl acetate was measured: $E_{415 m\mu}^{40\% EtOH}$=0.041. Estimation of this crude dl-α-tocopheryl acetate by liquid chromatography with the use of n-nonane as the standard indicated that its purity was 93.8% and the yield was 95.0%.

EXAMPLES 5 to 8

As shown in Table 1, TMHQ, metallic tin powder and a Friedel-Crafts catalyst in a predetermined amount were suspended in 15 ml of dichloroethane. A solution of a predetermined amount of phytyl chloride in 10 ml of dichloroethane was dripped into said suspension over a period of 2.5 hours under agitation and reflux in an atmosphere of nitrogen. Metallic tin powder in a predetermined amount was added to the suspension, and agitation and reflux was continued for another 2.5 hours. 11.5 ml of acetic anhydride and 0.22 g of γ-picoline were added to the reaction mixture, and the mixture was subjected to reflux for 1 hour. The lower boiling fractions were distilled off from the reaction mixture under reduced pressure. To the residue thus obtained was added n-hexane and an aqueous solution containing 2% sodium hydrosulfite, and the solution was filtered and separated. The hexane layer was washed 3 times with an aqueous solution of 2% sodium hydrosulfite and dried with anhydrous magnesium sulfate. The magnesium sulfate was filtered from the reaction mixture, which was concentrated and dried to obtain substantially achromatic dl-α-tocopheryl acetate. The following Table 1 illustrates the absorbance E of the crude While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for the preparation of dl-α-tocopherol, comprising condensing trimethylhydroquinone with phytyl halide in a chlorinated lower aliphatic hydrocarbon solvent selected from the group consisting of 1,2-dichloroethane and 1,1,2-trichloroethylene, in the presence of a catalytic amount of metallic tin and a Friedel-Crafts catalyst.

2. The method as defined by claim 1, wherein said phytyl halide is phytyl chloride.

3. The method as defined by claim 1, wherein the amount of chlorinated lower aliphatic hydrocarbon solvent present is about 2 to 100 times the weight of the trimethylhydroquinone.

4. The method as defined by claim 3, wherein said amount of chlorinated lower aliphatic hydrocarbon solvent is about 5 to 20 times the weight of the trimethylhydroquinone.

5. The method as defined by claim 1, wherein the amount of Friedel-Crafts catalyst present is in the range of 0.001 to 0.1 mol equivalent of the trimethylhydroquinone.

6. The method as defined by claim 5, wherein said amount of Friedel-Crafts catalyst present is in the range of 0.001 to 0.02 mol equivalent of the trimethylhydroquinone.

7. The method as defined by claim 1, wherein the amount of metallic tin present is in the range of 0.02 to 1.0 mol equivalent of the trimethylhydroquinone.

8. The method as defined by claim 7, wherein said amount of metallic tin present is in the range of 0.05 to 0.4 mol equivalent of the trimethylhydroquinone.

9. The method as defined by claim 1, wherein the reaction temperature is in the range of 40° to 150° C.

10. The method as defined by claim 1, wherein the Friedel-Crafts catalyst is selected from the group consisting of zinc chloride, aluminum chloride, boron trifluoride etherate, iron chloride, and tin chloride.

11. The method as defined by claim 1, further comprising washing and concentrating the resultant dl-α-tocopherol.

12. The method as defined by claim 1, further comprising acetylating the resultant dl-α-tocopherol.

* * * * *